US00PP21360P2

(12) United States Plant Patent
Leenders

(10) Patent No.: US PP21,360 P2
(45) Date of Patent: Oct. 5, 2010

(54) ***HEDERA HELIX* PLANT NAMED 'MAGIC DUST'**

(50) Latin Name: *Hedera helix*
Varietal Denomination: Magic Dust

(76) Inventor: Mark H. Leenders, Oudedyk 16, NZ Helden (NL) 5988

( * ) Notice: Subject to any disclaimer, the term of this patent is extended or adjusted under 35 U.S.C. 154(b) by 0 days.

(21) Appl. No.: 12/454,617

(22) Filed: May 20, 2009

(51) Int. Cl.
*A01H 5/00* (2006.01)

(52) U.S. Cl. ..... Plt./249

(58) Field of Classification Search ..... Plt./249
See application file for complete search history.

(56) References Cited

OTHER PUBLICATIONS

GrowIt- Wholesale Nursery Growers—"Ivy: Gold Dust English Ivy-Hedera helix 'Gold Dust'" http://web.archive.org/web/20050430044720/http://www.growit.com/plants/growers/(1 page total).*

* cited by examiner

*Primary Examiner*—Susan B McCormick Ewoldt
(74) *Attorney, Agent, or Firm*—Audrey Charles

(57) ABSTRACT

A new and distinct cultivar of *Hedera helix* plant named 'Magic Dust', characterized by its dark green with gray-green colored foliage having golden variegation, bronze-colored stems, and good garden performance.

2 Drawing Sheets

Latin name of genus and species of plant claimed: *Hedera helix* Plant Named 'Magic Dust'.

Variety denomination: 'Magic Dust'.

BACKGROUND OF THE INVENTION

The present invention relates to a new and distinct cultivar of *Hedera* plant botanically known as *Hedera helix,* commonly known as ivy, and hereinafter referred to by the cultivar name 'Magic Dust'.

The new *Hedera* cultivar is a naturally-occurring sport of a plant the *Hedera helix* 'Halebob'. 'Halebob' is a crinkly-leaf ivy having dark green-colored foliage with margins of bright gold, and it maintains its coloration throughout the year. The new cultivar was discovered in 2005 as a branch mutation of 'Halebob' in an outdoor nursery location in Helden, The Netherlands.

Asexual reproduction of the new *Hedera* by cuttings in a controlled environment in Helden, The Netherlands since 2006, has shown that the unique features of this new *Hedera* are stable and reproduced true to type in successive generations.

SUMMARY OF THE INVENTION

The following characteristics of the new cultivar have been repeatedly observed . . . and can be used to distinguish 'Magic Dust' as a new and distinct cultivar of *Hedera* plant:

1. Dark green with gray-green colored foliage having golden variegation;
2. Bronze-colored stems; and
3. Good garden performance.

Of the many commercially available *Hedera* cultivars, the most similar in comparison to the new cultivar is the parent cultivar 'Halebob', not patented. However, in comparison, plants of the new cultivar differ from its parent, in foliage color and growth habit. The new cultivar has a slightly different foliage color and shorter internodes making it more compact than the parent cultivar. It is ideal for ground cover, hanging baskets, planters or for climbing up a low wall.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Magic Dust'. The plants were grown in an outdoor nursery environment in 15 cm containers for approximately 2 years in Helden, The Netherlands. Plants were held in a glass-covered greenhouse during the winter months.

The photograph on the first sheet is a side perspective view of typical plants of 'Magic Dust' grown in an outdoor nursery.

The photograph at the top of the second sheet is a close-up view of typical young foliage of 'Magic Dust'.

The photograph at the bottom of the second sheet is a close-up view of typical mature foliage of 'Magic Dust'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in April 2008 under natural light conditions in Helden, The Netherlands when day temperatures ranged from 12° C. to 35° C. (53° ° F. to 95° F.) and night temperatures ranged from 6° C. to 18° C. (43° F. to 64° F.).

Plants used in the following description were grown in Helden, The Netherlands, in an outdoor nursery environment in 15 cm containers under conditions which closely approximate commercial production conditions. Plants were held in a glass-covered greenhouse during the winter months. The plants were grown for approximately 2 years when the description was taken. Measurements and numerical values represent averages of typical plants.

Botanical classification: *Hedera helix* cultivar Magic Dust.

Parentage: Sport of *Hedera helix* cultivar Halebob.

Propagation:

*Type.*—Cutting.

*Time to initiate roots in summer.*—Approximately 15 days at temperatures of approximately 20° to 25° C.

*Time to initiate roots in winter.*—Approximately 27 days at temperatures of approximately 18° to 22° C.

*Time to produce a rooted plant in summer.*—Approximately 27 days at temperatures of approximately 20° to 25° C.

*Time to produce a rooted plant in winter.*—Approximately 47 days at temperatures of approximately 18° to 22° C.

*Root description.*—White in color, medium thickness, fleshy.

*Rooting habit.*—Dense, freely branching.

Plant description:

*Growth habit and general appearance.*—Perennial spreading vine, moderate growth rate and moderate vigor.

*Crop time.*—Approximately 12 months from a rooted cutting to finish in an 11 cm container.

*Size.*—Plant height: Approximately 11.1 cm. Plant width (spread): Approximately 35.4 cm.

*Branching habit.*—Freely basal branching. Pinching not required, but will improve basal branching. Quantity: Approximately 15.

*Branches.*—Strength: Strong. Shape: Rounded. Appearance: Moderately glossy. Length: Approximately 19.0 cm. Diameter: Approximately 2.5 mm. Internode length: Approximately 2.1 cm. Texture: Glabrous. Color of young stems: 147A with an overlay of 187A resulting in a bronze appearance. Color of mature stems: N199A with an overlay of 187A resulting in a bronze appearance.

Foliage description:

*General description.*—Quantity of leaves per main stem: Approximately 9. Fragrance: None detected. Form: Simple. Arrangement: Alternate.

*Leaves.*—Shape: Palmately lobed, overall shape deltoid. Appearance: Glossy. Margin: Undulate. Apex: Acute. Base: Hastate. Venation pattern: Laciniate. Length of mature leaf: Approximately 3.2 cm. Width of mature leaf: Approximately 2.9 cm. Texture of upper and lower surfaces: Glabrous. Color of upper surface of young foliage: 139A with an irregular margin of 151C to 151D. Color of lower surface of young foliage: 138B with an irregular margin of 151D. Color of upper surface of mature foliage: 139A with occasional small blotches of 191A, an irregular margin of 5B to 5C, and venation of 191A. Color of lower surface of mature foliage: 191A with an irregular margin of 5D and venation of 143A to 143B.

*Petiole.*—Length: Approximately 4.3 mm. Width: Approximately 2.0 mm. Texture: Glabrous. Color: 146A with an overlay of 187A at base.

Flower and seed production: Not available, flower and seed production have not been observed.

Disease and pest resistance: Plants of the new *Hedera* have not been noted to be resistant to pathogens and pests common to *Hedera.*

Weather tolerance: Plants of the new *Hedera* have been observed to be moderately to highly tolerant to rain and wind. Plants of the new *Hedera* have been observed . . . to tolerate high temperatures of about 35° C. (95° F.) and to be hardy to a least USDA Zone 6.

What is claimed is:

1. A new and distinct cultivar of *Hedera helix* plant named 'Magic Dust', substantially as herein shown and described.

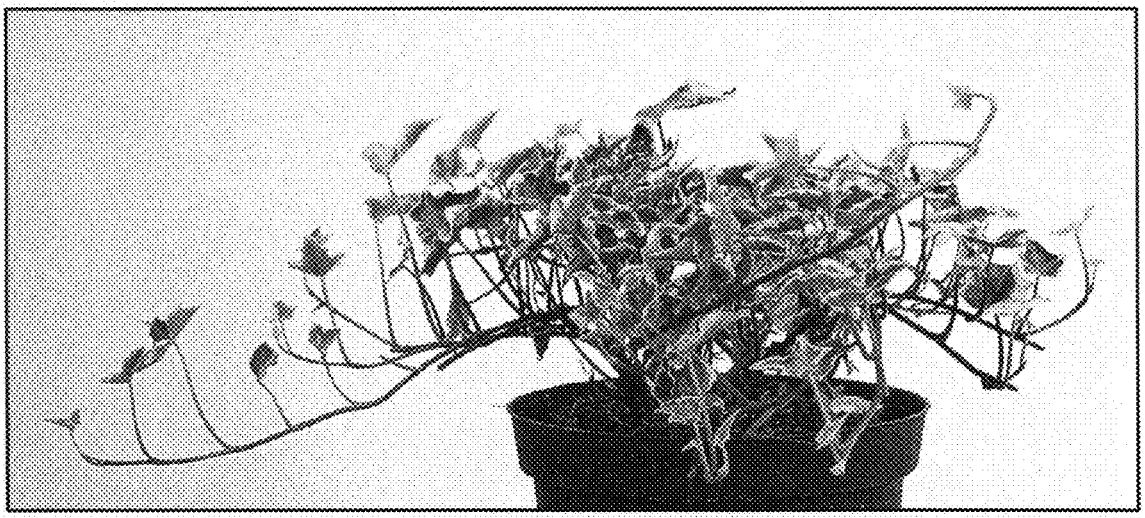

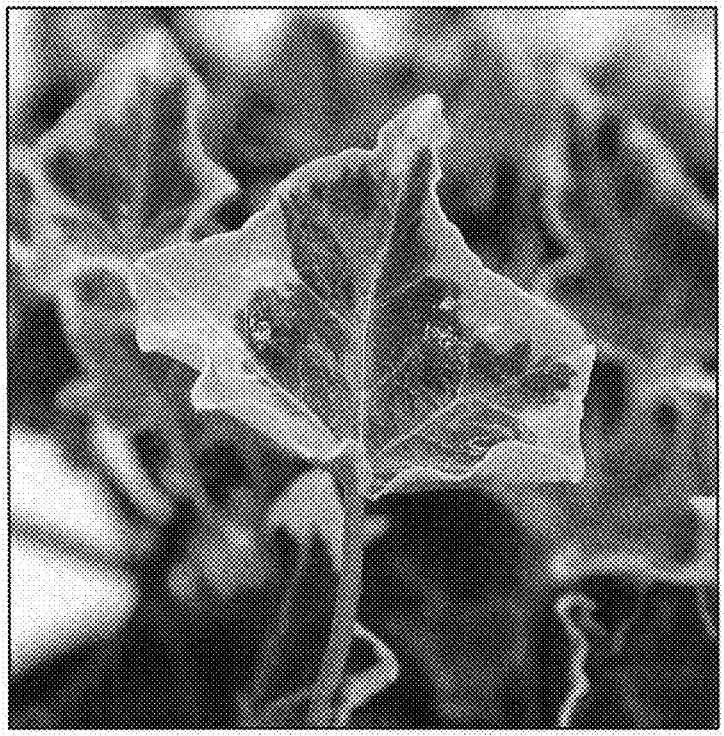
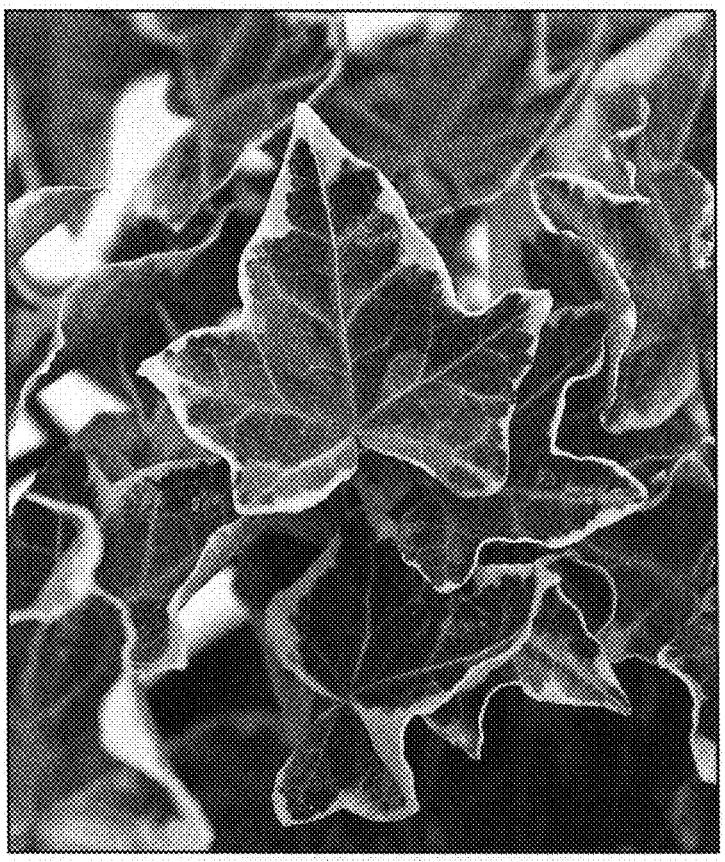

* * * * *